(12) United States Patent
Berendsen

(10) Patent No.: US 6,987,124 B2
(45) Date of Patent: *Jan. 17, 2006

(54) USE OF SEROTONERGIC COMPOUND FOR A METHOD OF TREATMENT OF HOT FLUSHES IN POST-MENOPAUSAL WOMEN

(75) Inventor: Hermanus Henricus Gerardus Berendsen, Oss (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/256,474

(22) Filed: Sep. 27, 2002

(65) Prior Publication Data

US 2003/0032646 A1    Feb. 13, 2003

Related U.S. Application Data

(62) Division of application No. 10/039,455, filed on Oct. 29, 2001, now Pat. No. 6,498,184.

(30) Foreign Application Priority Data

Dec. 5, 2000    (EP) .................................. 00204378

(51) Int. Cl.
  *A61K 31/40*    (2006.01)
  *A61K 31/495*    (2006.01)
(52) U.S. Cl. ...................... 514/428; 514/255; 514/408
(58) Field of Classification Search ................ 514/247, 514/252.16, 408, 255, 428
  See application file for complete search history.

(56) References Cited

U.S. PATENT DOCUMENTS 4,971,969 A * 11/1990 Carlier et al. ............... 514/252
6,498,184 B2 * 12/2002 Berendsen .................. 514/428

FOREIGN PATENT DOCUMENTS

EP    0 370 560 A    5/1990
EP    0 863 136 A    9/1998
EP    0 943 329 A    9/1999
WO    WO 99/43647    *    9/1999

OTHER PUBLICATIONS

Berendsen, H.H.: "The Role of Serotonin in Hot Flushes", MATURITAS, (Oct. 31, 2000) 36 (3) 155-64, Abstract, pp. 159-160.

Loprinzi et al: "Preliminary Data from a Randomized Evaluation of Fluoxetine (Prozac) for Treating Hot Flashes in Breast Cancer Survivors", Breast Cancer Research Treatment, vol. 57, No. 1, 1999, p. 34, Abstract Only.

Goodnick et al: "Selective Serotonin Reuptake Inhibitors in Affective Disorders -I. Basic Pharmacology", Journal of Psychopharmacology, vol. 12, No. 3, 1998, pp. S5-S20. Abstract, p. S8, right-hand column, paragraph 2.

Jenck et al: "Antiaversive Effects of $5HT_{2C}$ Receptor Agonists and Fluoxetine in a Model of Panic-Like Anxiety in Rats", European Neuropsychopharmacology, vol. 8, No. 3 (1998), pp. 161-168.

Trott, M.D. et al: "An Open Trial of Sertraline for Menopausal Hot Flushes: Potential Involvement of Serotonin in Vasomotor Instability" Delaware Medical Journal, US, Wilmington,DE, vol. 69, No. 9, Sep. 1997, pp. 481-482.

* cited by examiner

Primary Examiner—Sreeni Padmanabhan
Assistant Examiner—Jennifer Kim
(74) Attorney, Agent, or Firm—William P. Ramey, III; F. Aaron Dubberley

(57) ABSTRACT

The present invention relates to a method of treatment of hot flushes with a $5\text{-HT}_{2C}$ receptor agonist and in particular to the use of the selective $5\text{-HT}_{2C}$ receptor agonists 1-[6-chloro-5-(trifluoromethyl)-2-pyridinyl]-piperazine and (S)-(+)-3-[(2,3-dihydro-5-methoxy-1H-inden-4-yl)oxy-pyrrolidine or pharmaceutically acceptable acid addition salts thereof for the manufacture of a pharmaceutical formulation adapted for the treatment of hot flushes.

1 Claim, No Drawings

USE OF SEROTONERGIC COMPOUND FOR A METHOD OF TREATMENT OF HOT FLUSHES IN POST-MENOPAUSAL WOMEN

This application is a divisional of U.S. application Ser. No. 10/039,455, filed on Oct. 29, 2001, now U.S. Pat. No. 6,498,184.

FIELD OF THE INVENTION

The invention relates to the use of a serotonergic compound for the treatment of hot flushes.

BACKGROUND OF THE INVENTION

The most well-known complaints of the (post)-menopausal syndrome are due to changes in temperature regulation, causing sudden crises of feelings of excessive body heat (hot flushes). These symptoms are highly disturbing for a large proportion of menopausal women, leading to therapy requests to the medical profession. Usually, replacement of estrogens is selected as remedy. Less commonly and more recently explored is the selection of non-hormonal compounds as medicine for treating hot flushes. For example, the use of serotonergic uptake inhibitors and serotonin (=5-hydroxy-tryptophan=5-HT) antagonists for the treatment of hot flushes is discussed in Berendsen, Maturitas Vol 36, pp 155–164, 2000. Some beneficial effects of $5-HT_{2A}$ antagonists and serotonin uptake inhibitors were reported. The beneficial effect of the serotonin reuptake inhibitors sertraline and paroxetine were described in Plouffe et al., Delaware Medical Journal 69: pp 481–482, 1997, Roth and Scher, Psycho-Oncology 7, pp 129–132, 1998, and Stearns et al., Annals of Oncology 11, pp 17–22, 2000.

SUMMARY OF THE INVENTION

It has now been found that an agonist for $5-HT_{2C}$ receptors in an organism can be used for a method of treatment of hot flushes.

DETAILED DESCRIPTION OF THE INVENTION

Unexpectedly, these $5-HT_{2C}$-agonists produce better results than SSRI's against hot flushes in view of the extent to which side effects are compensated for by efficacy.

Thus, the invention provides for a method of treatment of hot flushes with a $5-HT_{2C}$ receptor agonist. In particular, a selective $5-HT_{2C}$ receptor agonist is preferred. A selective $5-HT_{2C}$ receptor agonist in the context of the description of this invention means a $5-HT_{2C}$ receptor agonist which is more active as agonist on $5-HT_{2C}$ receptors than on other 5-HT receptor subtypes, such as $5-HT_{1A}$, $5-HT_{2A}$ and/or $5-HT_3$ receptors. The selective $5-HT_{2C}$ receptor agonist should preferably be such that it is at least 5 times more active on $5-HT_{2C}$ receptors than on the other serotonin receptors. The 5-HT agonists described in EP 370 560 are particularly suitable for the use of this invention. Specifically 1-[6-chloro-5-(trifluoromethyl)-2-pyridinyl]-piperazine and its pharmaceutically acceptable acid addition salts have the most desirable properties out of this group for the use of this invention. More preferred is the use of a $5-HT_{2C}$ agonist being at least 10 times more active on $5-HT_{2C}$ receptors relative to $5-HT_{2A}$ receptors. Most preferred is the use of the azetidines or pyrrolidine compounds disclosed in EP863136 for use in the treatment of hot flushes, and in particular the compound (S)-(+)-3-[(2,3-dihydro-5-methoxy-1H-inden-4-yl)oxy-pyrrolidine or its pharmaceutically acceptable acid addition salts described in that disclosure.

Since the treatment of the present invention is not based on hormone replacement these treatment agents are preferably used in those circumstances were treatment with a hormone or a hormone receptor agonist bears higher risks. Therefore, an aspect of this invention is that it makes a treatment available for hot flushes in patients at risk for hormone dependent tumour growth. Such patients are the group of patients with ovariectomy in view of estrogen dependent tumour growth. Another aspect of the invention is that it makes a treatment available for hot flushes in patients with adverse feminizing responses to estrogens. In particular, male patients functionally or pharmacologically castrated for the purpose of removing endogenous hormones can be treated for hot flushes with $5-HT_{2C}$-agonists.

Hot flushes not only occur as complaint during menopause, but also in certain women during specific points in time of the menstrual cycle, for example before and during the days of menstruation. It is an aspect of this invention that hot flushes in those circumstances can be very well non-hormonally treated with a $5-HT_{2C}$ agonist.

The terms used in this description have the meaning according to common understanding of these terms. The accepted use of the terminology to indicate serotonin receptor subtypes is for example used in Barnes and Sharp, Neuropharmacology 38, pp 1083–1152, 1999. A serotonergic compound is a compound which directly or indirectly, for example as agonist or as serotonin reuptake inhibitor activates serotonin receptors in an organism. An agonist for a receptor is a compound which produces an effect caused by conformational changes of the receptor by direct binding to the receptor. For the $5-HT_{2C}$ receptor the agonist mimicks at least partially the effect of serotonin. Thus, a partial agonist is explicitly included within the scope of this invention. It is in many circumstances beneficial to use a partial agonist rather than a full agonist. The former might be less efficacious but may have less risk for full-blown adverse overdose effects.

Determination of selectivity of a receptor agonist can be done by methods well known in the art. The basic technique is with binding experiments in which the compound is tested for binding affinity to the subtypes of receptors. Alternatively, selectivity can be determined with in vitro expression systems in which a biochemical parameter, such as cyclic adenosine monophosphate or phosphoinositol production or inhibition is used to determine receptor activation by an agonist. In vivo methods can also be used when selective models for testing receptor stimulation are available. Some differences in the selectivity results obtained with these methods can occur. Usually, and under the condition that the test is accepted as reliable, the in vivo selectivity is the preferred indicator for determination of selectivity of a compound over in vitro methods. Results with in vitro expression of receptor activity are in turn more preferred for determination of the selectivity than binding experiments. For a suitable collection of techniques to determine the properties of a $5-HT_{2C}$ agonist reference is made to Martin et al., $5-HT_{2C}$ receptor agonists: Pharmacological characteristics and therapeutic potential. J. Pharmacol & Experimental Therapeutics 286: 913–924, 1998

The present invention further includes the use of a $5-HT_{2C}$-agonist for the manufacture of a medicament for the treatment of hot flushes.

Suitable acid addition salts include hydrochloric, fumaric, maleic, citric or succinic acid, these acids being mentioned only by way of illustration and without implied limitation. A preferred salt is the hydrochloric acid salt.

The amount of a 5-HT$_{2C}$ agonist, also referred to herein as the active ingredient, which is required to achieve a therapeutic effect will, of course, vary with the particular compound, the route of administration and the age and other conditions of the recipient.

A suitable daily dose for any of the two compounds chemically named above will be in the range of 5 to 140 mg of the base per person per day, preferably in the range of 20 to 70 mg of the base per recipient per day. In the case of tolerance development, treatments can be further optimalised by increasing the dose up to 5 times in the course of a chronic treatment in humans. The desired dose may be presented as one, two, three or more sub-doses administered at appropriate intervals throughout the day.

While it is possible for the active ingredient to be administered alone, it is preferable to present it as a pharmaceutical formulation. Accordingly, the present invention further provides a pharmaceutical formulation for use in the treatment of hot flushes comprising a 5-HT$_{2C}$-agonist, together with a pharmaceutically acceptable carrier thereof and optionally other therapeutic agents. The carrier must be "acceptable" in the sense of being compatible with the other ingredients of the formulation and not deleterious to the recipients thereof. The invention further includes a pharmaceutical formulation, as hereinbefore described, in combination with packaging material suitable for the pharmaceutical formulation, said packaging material including instructions for the use of the pharmaceutical formulation in the treatment of hot flush.

Formulations include those suitable for oral, rectal, nasal, topical (including transdermal, buccal and sublingual), vaginal or parenteral (including subcutaneous, intramuscular, intravenous, intradermal and epidural) administration. The formulations may be prepared by any methods well known in the art of pharmacy, for example, using methods such as those described in Gennaro et al., Remington's Pharmaceutical Sciences (18th ed., Mack Publishing company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as tablets or capsules each containing a predetermined amount of active ingredient; as a powder or granulates; as a solution or suspension. The active ingredient may also be presented as a bolus or paste, or may be contained within liposomes or microparticles.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

Formulations may, for example, be presented in a suitable sustained release form, for example, in a device such as the Minipump™.

The compounds according to the present invention are non-toxic.

The the compounds 1-[6-chloro-5-(trifluoromethyl)-2-pyridinyl]-piperazine and (S)-(+)-3-[(2,3-dihydro-5-methoxy-1H-inden-4-yl)oxy-pyrrolidine, and their pharmaceutically acceptable acid addition salts may be prepared by any method known in the art for the preparation of a compound of similar structure. Typically the compound 1-[6-chloro-5-(trifluoromethyl)-2-pyridinyl]-piperazine can be prepared by the methods described in EP 370 560, the contents of which are incorporated herein by reference, whereas the compound (S)-(+)-3-[(2,3-dihydro-5-methoxy-1H-inden-4-yl)oxy-pyrrolidine and its pharmaceutically acceptable acid addition salts can be prepared by the methods described in EP863136, the contents of which are incorporated herein by reference.

The following example is for illustration and should not be considered to be limiting in anyway:

EXAMPLE

A test for demonstration of the effect of compounds on an acute increment of body heat production representative for hot flushes in humans is based on telemetric body temperature measurements in freely moving rats.

Method

Male rats (HSD/Cpb:WU, Harlan Sprague Dawley, Zeist, The Netherlands), weighing 350–480 g, were used. The rats were implanted with a Physio Tel TA11CTA-F40 Implant (Data Sciences International) under pentobarbital anaesthesia. After surgery the rats were housed individually in a type II clear Macrolon™ cage (23×17×x14 cm). The cages were placed on receivers (RLA 1020). After a recovery and adaptation period of at least one week the rats were used for the experiments. On the experimental day, body temperature, heart rate and locomotor activity was monitored for 30 minutes prior to injection of vehicle or test compound. This period provides a baseline core body temperature relative to which the changes of body temperature after the manipulation of the rats for injection are expressed. After 30 minutes the rats were injected subcutaneously with vehicle or test compound and the same parameters were measured for at least 60 minutes. Immediately after injection the core body temperature rises. Compounds inhibiting this rise in temperature reveal an inhibiting effect on acute body heat production. Results obtained with other parameters, such as the effect on heart rate and on locomotor activity are not presented here. 6 animals were used for measurement of each dose of compound Compounds tested are:
1-[6-chloro-5-(trifluoromethyl)-2-pyridinyl]-piperazine HCl, which is indicated as Org 12962.
(S)-(+)-3-[(2,3-dihydro-5-methoxy-1H-inden-4-yl)oxy-pyrrolidine HCl, which is indicated as Org 37684.
Fluoxetine HCl Data were analysed using Dataquest IV Data Acquisition System Ver 2.2. Compounds were dissolved in NaCl 0.9% (m/v) in water as vehicle for subcutaneous injection.

TABLE 1

Effect of Org 37684 on temperature increments after manipulation of the rats relative to the body temperature during 30 minutes prior to the manipulation.

| | Org 37684 | Org 37684 | Org 37684 | Org 37684 |
|---|---|---|---|---|
| Dose:<br>Time[1] | 0 mg/kg | 1.0 mg/kg | 2.2 mg/kg | 4.6 mg/kg |
| 5 | 0.50[2] | 0.29 | 0.41 | 0.00 |
| 10 | 0.69 | 0.68 | 0.47 | −0.03 |
| 15 | 0.79 | 0.78 | 0.44 | −0.13 |
| 20 | 0.80 | 0.58 | 0.40 | −0.20 |
| 25 | 0.81 | 0.69 | 0.24 | −0.14 |
| 30 | 0.60 | 0.63 | 0.13 | −0.24 |
| 35 | 0.40 | 0.49 | 0.04 | −0.24 |
| 40 | 0.41 | 0.40 | −0.05 | −0.27 |
| 45 | 0.30 | 0.20 | −0.09 | −0.34 |
| 50 | 0.27 | 0.14 | −0.21 | −0.40 |
| 55 | 0.24 | 0.34 | −0.26 | −0.43 |
| 60 | 0.20 | 0.14 | −0.25 | −0.33 |

[1] is time after injection in minutes
[2] numbers in the tables represent absolute mean increments in body temperature in ° C. for 6 rats relative to baseline during 30 minutes prior to manipulation of the animals.

TABLE 2

Effect of Org 12962; explanation as for table 1

| | Org 12962 | Org 12962 |
|---|---|---|
| Dose:<br>Time | 0 mg/kg | 2.0 mg/kg |
| 5 | 0.90 | 0.12 |
| 10 | 1.06 | 0.10 |
| 15 | 1.03 | 0.06 |
| 20 | 0.92 | −0.03 |
| 25 | 0.93 | −0.05 |
| 30 | 0.83 | −0.14 |
| 35 | 0.81 | −0.19 |
| 40 | 0.72 | −0.23 |
| 45 | 0.66 | −0.19 |
| 50 | 0.65 | −0.24 |
| 55 | 0.51 | −0.25 |
| 60 | 0.41 | −0.16 |

TABLE 3

Effect of fluoxetine; explanation as for table 1

| | Fluoxetine | Fluoxetine |
|---|---|---|
| Dose:<br>Time | 0 mg/kg | 22 mg/kg |
| 5 | 0.72 | 0.28 |
| 10 | 0.96 | 0.59 |
| 15 | 0.97 | 0.71 |
| 20 | 0.90 | 0.72 |
| 25 | 0.89 | 0.66 |
| 30 | 0.80 | 0.56 |
| 35 | 0.69 | 0.55 |
| 40 | 0.65 | 0.45 |
| 45 | 0.53 | 0.38 |
| 50 | 0.41 | 0.27 |
| 55 | 0.33 | 0.29 |
| 60 | 0.18 | 0.85 |

Interpretation of Results:

The rise in body temperature of up to slightly less than 1° C. within the period of 60 minutes after manipulation for injecting the animals was prevented by Org 12962 or by Org 37684, but not by fluoxetine. The prevention of temperature rise was statistically significant for the two 5-HT$_{2C}$ agonists with the ANOVA/MANOVA Tukey HSD test on sample points. The results are interpreted to indicate that 5-HT$_{2C}$ agonists counteract acute increments in body temperature such as those which occur during a hot flush.

What is claimed is:

1. A method for the treatment of hot flushes in postmenopausal women comprising the step of administering an effective amount of a selective 5-HT$_{2C}$ receptor agonist and a pharmaceutically acceptable carrier.

* * * * *